(12) United States Patent
Leplanquais et al.

(10) Patent No.: US 8,241,676 B2
(45) Date of Patent: Aug. 14, 2012

(54) **USE OF A *LIMNOPHILA* EXTRACT AS A COSMETIC AGENT, AND COSMETIC COMPOSITION CONTAINING SAME**

(75) Inventors: Virginie Leplanquais, Fay-aux-Loges (FR); Virginie Pecher, La Chapelle Saint Mesmin (FR); Marc C M Dumas, Saint Jean le Blanc (FR); Krystell Lazou, Orléans (FR)

(73) Assignee: LVMH Recherche, Saint Jean de Braye (FR)

( * ) Notice: Subject to any disclaimer, the term of this patent is extended or adjusted under 35 U.S.C. 154(b) by 386 days.

(21) Appl. No.: 12/477,479

(22) Filed: Jun. 3, 2009

(65) Prior Publication Data

US 2009/0304613 A1    Dec. 10, 2009

(30) Foreign Application Priority Data

Jun. 6, 2008 (FR) ...................................... 08 53797

(51) Int. Cl.
*A61K 36/00* (2006.01)
(52) U.S. Cl. ..................................................... 424/725
(58) Field of Classification Search ........................ None
See application file for complete search history.

(56) References Cited

U.S. PATENT DOCUMENTS

| 4,835,148 | A  | * | 5/1989 | Barford et al. | 514/179 |
| 6,124,362 | A  | * | 9/2000 | Bradbury et al. | 514/569 |
| 6,410,593 | B1 | * | 6/2002 | De Mesanstourne et al. | 514/556 |
| 6,451,300 | B1 | * | 9/2002 | Dunlop et al. | 424/70.27 |

FOREIGN PATENT DOCUMENTS

WO   2006069192   6/2006

OTHER PUBLICATIONS

Search Report dated Mar. 13, 2009 from French Application No. 0853797.

Reddy et al.; Chemical and Pharmacological Investigations of *Limnophila conferta* and *Limnophila heterophylla*; International Journal of Pharmacognosy, vol. 29, No. 2, 1991, pp. 145-153.
Bosset et al.; Decreased expression of keratinocyte Beta1 integrins in chronically sun-exposed skin in vivo; British Journal of Dermatology 2003, 148:7770-7778.
Deveraux et al.; IAP Family proteins—suppressors of apoptosis; Genes & Development; 13 (1999), pp. 239-252.
Grossman et al.; Transgenic expression of survivin in keratinocytes counteracts UVB-induced apoptosis and cooperates with loss of p53; Journal of Clinical Investigation; 2001, 108:991-999.
Jones et al.; Separation of Human Epidermal Stem Cells from Transit Amplifying Cells on the Basis of Differences in Integrin Function and Expression; Cell 1993, vol. 73, pp. 713-724.
Kaur; Interfollicular Epidermal Stem Cells: Identification, Challenges, Potential; Journal of Investigative Dermatology (2006), vol. 126, pp. 1450-1458.
Kukongviriyapan et al.; Antioxidant and Vascular Protective Activities of *Cratoxylum formosum*, *Syzygium gratum* and *Limnophila aromatica*; Biol. Pharm. Bull.; 30(4), pp. 661-666; 2007.
Marconi et al.; Survivin Identifies Keratinocyte Stem Cells and Is Downregulated by Anti-Beta1 Integrin During Anoikis; Stem cells 2007, 25:149-155.
Snyder, L.R.; Classification of the solvent properties of common liquids; Journal of Chromatography, 92(1974), pp. 223-230.
Vader et al; Surivivin mediates targeting of the chromosomal passenger complex to the centromere and midbody; EMBO Reports, 2006, 7, 1, pp. 85-92.
Varlet et al.; Age-Related Functional and Structural Changes in Human Dermo-Epidermal Junction Components; Journal Investigative Dermatology;symp Proc; 1998, 3:172-179.
Xie et al.; A study of using tissue-engineered skin reconstructed by candidate epidermal stem cells to cover the nude mice with full-thickness skin defect; Journal of Plastic, Reconstructive & Aesthetic Surgery; 2007, 60(9):983-990.
Zuliani et al.; Apoptosis and Proliferation during Human Epidermal Aging after an Acute UV Exposure: and in vivo Immunohistological Study; J Invest Dermatology 2004, 123:2, A50, 302.

\* cited by examiner

*Primary Examiner* — Christopher R. Tate
*Assistant Examiner* — Deborah A. Davis
(74) *Attorney, Agent, or Firm* — Woodcock Washburn LLP

(57) ABSTRACT

The invention relates to the use of a plant extract of a plant of the *Limnophila* genus, in particular an extract of the plant species *Limnophila conferta*, as a cosmetic agent or as an active agent in cosmetic compositions.

21 Claims, No Drawings

USE OF A *LIMNOPHILA* EXTRACT AS A COSMETIC AGENT, AND COSMETIC COMPOSITION CONTAINING SAME

CROSS-REFERENCE TO RELATED APPLICATIONS

This applications claims the benefit of French Application No. 0853797, filed Jun. 6, 2008, the entirety of which is incorporated herein.

TECHNICAL FIELD

The present invention relates to the use of an extract of plants belonging to the *Limnophila* genus as a cosmetic agent and to a cosmetic composition containing same. More particularly, the subject of the invention is the use of an extract of the plant species *Limnophila conferta* as a cosmetic agent, and the use thereof as an active agent in cosmetic compositions, and also the cosmetic care methods using said compositions.

BACKGROUND

Apoptosis is an active biological process of elimination, by fragmentation, of certain cells of the organism.

It constitutes a programmed elimination of cells at the biological tissue level, under genetic control. The elimination may be natural (surplus cells in the tissue) or induced by various forms of stress.

The biological cascade of apoptosis is known and uses a number of effectors such as caspases, in particular the effector caspases 3 or 7, which will implement the apoptosis programme, and the initiating caspases 8 and/or 9, which will trigger it.

A certain number of apoptosis inhibitors are also known (Deveraux et al., *Genes Dev.* 13 (1999), pp. 239-252), among which is survivin. These inhibitors therefore regulate cell survival, thus participating in cell homeostatis in biological tissues.

Survivin, the only member of the IAP (Inhibitor of Apoptosis Protein) family, is a bifunctional protein capable both of balancing the apoptosis of cells and of regulating the cell cycle thereof.

Survivin inhibits in particular the activation of certain caspases, in particular caspases 3, 7 and 9.

This protein is expressed in strongly growing embryonic tissues, but is not expressed in adult differentiated tissues, except in tissues that have a physiological cell renewal and/or are involved in a repair process. Thus, at the cutaneous level, it is most particularly expressed in the keratinocytes of the basal layer of the epidermis, which provide formation and renewal of the latter.

It is in this basal layer that the epidermal stem keratinocytes are found, these being cells with a high potential for regeneration of this tissue, which have been demonstrated to be the most effective in forming a complete epidermis (J L Xie et al., *J Plast Reconstr. Aesthet. Surg.* 2007; 60(9); 983-90).

Now, it has been shown that survivin is mainly expressed in the stem cells of the epidermis (Marconi A, Dallaglio K, Lotti R, Vaschieri C, Truzzi F, Fantini F, Pincelli C, Stem cells 2007: 25: 149-155).

Conversely, overexpression of survivin shows a significant decrease in the number of apoptotic cells in the epidermis after exposure to ultraviolet radiation (Grossman et al., 2001 *J Clin Invest* 108; 991-999).

It has also been demonstrated that the inactivation of beta-1 integrins completely abolishes the cellular expression of survivin (Marconi A et al., Stem cells 2007: 25: 149-155) and leads the cells to apoptosis.

Beta-1 integrins are adhesion proteins through which the keratinocytes of the epidermal basal layer adhere to the proteins of the dermal-epidermal junction.

Beta-1 integrins are expressed more strongly by the stem cells of the epidermis (P. Jones, *Cell* 1993, 73: 713-724, Kaur *J Invest Dermatol* 2006, 126, 1450-1458), which corroborates the observation of a stronger expression of survivin in these cells.

Now, during ageing, a drop in the expression of beta-1 integrins in the keratinocytes (B Le Varlet et al. *J Investig Dermatol Symp Proc.* 1998, 3; 172-179) and in the wrinkled skin areas exposed to light (S Bosset et al. *British J Dermatol* 2003, 148; 7770-778) is observed.

Thus, the proteins which ensure maintenance of survivin in the basal cells of the epidermis decrease with age, and, in parallel, an increase in the sensitivity of the cells to apoptosis and a decrease in cycling cells are observed (Zuliani et al., *J. Invest. Dermatol.* 2004, 123:2, A50, 302), these observations converging to indicate a probable survivin deficiency in ageing skin.

In addition to its apoptosis-regulating role, survivin has been identified as a constituent of the "chromosomal passenger complex" which coordinates the chromosomes with the cytoskeleton during mitosis (Vader et al., EMBO reports, 2006, 7, 1, 85-92); it therefore plays an essential role in normal cell division, this division being impaired during ageing with, as a consequence, less renewal of the epidermis, thinning thereof, and the development of wrinkles.

Survivin is therefore a regulator of the survival and of the resistance of keratinocytes; it acts by modulating the sensitivity of apoptosis of the keratinocytes located in the basal layer of the epidermis, including the stem cells. It also regulates their capacity for renewal and for regeneration of the epidermis.

It thus makes it possible to spare the cell stock of the epidermis and to maintain efficient epidermal cell renewal.

Document WO 2006/069192 (GILLETTE Co) discloses the use, in cosmetics, of survivin-inhibiting agents for a hair and body-hair growth reduction effect.

To date, no compounds that act as survivin-expression stimulators have been described for uses in dermatology or cosmetics.

Authors have described the antioxidant and free-radical-scavenging effect of an aqueous extract of *Limnophila aromatica* administered orally to rats (Kukongviriyapan et al., *Biol. Pharm Bull.* 2007 30 (4) 661-666).

Authors have studied alcoholic extracts of *Limnophila conferta* and *Limnophila heterophylla*, administered orally to rats, and have concluded therefrom that these alcoholic extracts have an advantageous activity in terms of wound healing but no significant activity on a model of acute inflammation (Reddy et al., *Int. J. Pharmacognosy* (1991), 29, 2 145-153).

However, to date, no data exists concerning the use of plant species belonging to the *Limnophila* genus, and more particularly the species *Limnophila conferta*, in the form of the product of any method of extraction, as an active agent in cosmetic or dermatological compositions.

SUMMARY

The present invention is directed to cosmetic compositions comprising a plant extract of a plant of the species belonging to the *Limnophila* genus, optionally in solution or in dispersion in a cosmetically acceptable carrier compatible with topical application to a body zone. Methods of using these compositions is also described.

DETAILED DESCRIPTION OF ILLUSTRATIVE EMBODIMENTS

Over the course of their studies, the inventors have demonstrated that an extract obtained from a plant material comprising or formed from at least one plant of the *Limnophila* genus, in particular of the plant species *Limnophila conferta*, activates or stimulates the expression of the survivin protein in the keratinocytes of the basal layer of the epidermis, and more particularly in the stem cells of said basal layer. Said extract thus plays a protective role with respect to the regenerative cells of the human epidermis, and most particularly the stem cells of the basal layer of the epidermis.

These extracts can thus be used as an active agent in cosmetic compositions, aimed in particular at preventing or delaying the appearance of the signs of skin ageing or reducing the effects thereof, or else at promoting cell or tissue longevity; at promoting the reconstruction of a damaged epidermis, in particular damaged by ultraviolet radiation, and also the healing of cutaneous wounds in normal skin and ulcerative wounds that heal poorly; at preventing or delaying hair loss, at accelerating or promoting hair regrowth or hair reinforcement; at promoting the growth of the nails and/or reinforcing the strength thereof, as an adjuvant for prolonging cell cultures in vitro for the purposes of cultured epidermis production (reconstructed epidermis) for therapeutic purposes, for example in grafts or else in maintaining purified populations of stem cells of the epidermis or hair follicles in vitro for therapeutic or research purposes.

A main purpose of the invention is to propose the use of a cosmetically acceptable plant extract obtained from plants, as a cosmetic agent.

Another purpose of the invention is the use of said extract as a cosmetic agent, or as an active agent in cosmetic compositions, and the cosmetic care methods using said compositions:

a) for preventing or delaying the appearance of the signs of skin ageing or slowing down the effects thereof, and/or b) for the care of or for reconstructing the epidermis or the stratum corneum thereof, notably when it is damaged, in particular by ultraviolet radiation, and/or c) for restoring the functioning of the hair cycle, in order to prevent or slow down hair loss, to accelerate or promote hair regrowth, in particular in the case of alopecia, or to reinforce brittle hair, and/or d) for promoting growth of the nail and/or reinforcing the strength thereof.

A further main purpose of the invention is to provide a cosmetic care method, using a cosmetically acceptable plant extract, in particular for carrying out the types of cosmetic care indicated above.

Finally, a further main purpose of the invention is to provide a method for the in vitro culture of stem cells and/or of cells with a high clonogenic potential for the purposes of fundamental studies or of production of cultured epidermis, such as reconstructed epidermis, for therapeutic purposes, for example, as in the case of a graft, following burns or ulcerative wounds which heal poorly, comprising the use of a plant extract that is acceptable with said cell culture, obtained from plants.

A first aspect of the present invention relates to a cosmetic agent comprising a plant extract obtained from a plant material formed by, or comprising, at least one plant, the species of which belongs to the *Limnophila* genus, in particular an extract obtained from a plant material formed by, or comprising, at least one plant of the plant species *Limnophila conferta*.

The plant material used may be the whole plant or a part of the plant, such as the root, the rhizome or an above-ground part, in particular the stem, the leaves, the flowers, the seeds or the floral buds.

The extract is preferably obtained from the above-ground parts of the plant, and in particular the stems and the leaves.

Prior to the extraction step itself, the plant material may have been dried and/or ground.

According to one preferred embodiment of the extraction, the plant material is in the dry and ground state.

In addition to the plants of the *Limnophila* genus, and in particular of the plant species *Limnophila conferta*, the plant material from which the extract of the invention is prepared may comprise one or more other plants, without distinction in the form of whole plants or of parts of a plant.

These plants may be of a genus other than the *Limnophila* genus, or plants of another family, known to have properties similar or complementary to those demonstrated for the plants of the *Limnophila* genus.

Plants of which the extracts are known to slow down or prevent the effects of skin ageing, by various mechanisms, such as maintaining the integrity of the skin structure or an action on wrinkles, may in particular be chosen.

The extract may be prepared by various extraction methods known to those skilled in the art.

However, the extraction is in particular carried out by bringing the selected plant material into contact with a polar solvent or a mixture of polar solvents.

According to the present invention, the expression "polar solvent" signifies that the solvent has a polarity index value P' which is greater than or equal to a value of 4.

The polarity index is a value calculated on the basis of thermodynamic values (of solubility and of change of state) which demonstrates the more or less polar nature of a molecule.

For the polarity indices of the solvents, reference will be made to the article by L. R. SNYDER; *Classification of the solvent properties of common liquids; Journal of Chromatography*, 92 (1974), 223-230, which is included in the present application by way of reference.

As polar solvent or mixture of polar solvents that can be used for the extraction step, a solvent or a mixture of solvents chosen from water, a $C_1$-$C_4$ alcohol, preferably chosen from ethanol or butanol, a glycol preferably chosen from glycerol, butylene glycol and propylene glycol, and mixtures thereof, will advantageously be chosen.

The preferred mixtures are mixtures of at least one alcohol and of water, or of at least one glycol and of water, comprising at least 10% v/v of alcohol or glycol, the remainder being made up of water.

Among these solvent mixtures, a mixture of water and of ethanol in a 50/50 v/v ratio, or a mixture of water and of butylene glycol in a 50/50 v/v ratio, is preferred.

The extraction step per se is preferably carried out by hot reflux for at least 30 minutes.

According to another variant of the invention, the extraction may also be carried out by a method using a polar solvent in the subcritical state, said solvent being advantageously water in the subcritical state.

The extraction may also optionally comprise an additional step comprising treatment of the plant material or of the plant extract, aimed at partially or completely discolouring it, or at purifying it.

This discolouring step may, for example, comprise treatment of the plant material prior to the extraction itself, or of the extract, with a solution of an apolar solvent or of a mixture of apolar solvents, preferably treatment with a $C_6$-$C_7$ alkane, for example heptane, or treatment comprising bringing the extract into contact with particles of active carbon, or alternatively treatment with $CO_2$ in the supercritical state.

The extraction may be completed by a step of partial or total elimination of the extraction solvents.

In the first case, the extract is generally concentrated until an aqueous concentrate devoid of significant amounts of organic solvent is obtained; in the second case, a dry residue is obtained.

Alternatively, the extract obtained may be in the form of a powder after lyophilization or atomization of the product of the step of extraction in the solvent or solvent mixture mentioned above.

The powder may be used as it is in a cosmetic or dermatological composition according to the invention, or may be redispersed in a solvent or solvent mixture.

In general, the product of the extraction step may be dissolved or dispersed in a solvent or solvent mixture, so as to be used as an active agent in the cosmetic or dermatological compositions of the invention.

The solvent or the solvent mixture in which the extract is dissolved or dispersed may be identical to or different from that having been used for the extraction.

The extract of the invention may also be adsorbed on to a support advantageously chosen from porous or nonporous nylon powders and micas or any lamellar mineral substance.

In this case, the extract used is preferably an aqueous extract.

A further aspect of the invention is the use of a plant extract of a plant of the species belonging to the *Limnophila* genus, preferably an extract of the plant species *Limnophila conferta*, as a cosmetic agent in cosmetic compositions.

The invention concerns in particular the use of the extract in a cosmetic composition, as one of the cosmetic agents, or as one of the active agents, for carrying out the types of cosmetic care mentioned above or in the following description for preventing or delaying the appearance of the signs of skin ageing or slowing down the effects thereof, and/or for the care of, or for reconstructing, the epidermis or the stratum corneum thereof, notably when it is damaged, in particular by ultraviolet radiation, and/or for restoring the functioning of the hair cycle, for preventing or slowing down hair loss, for accelerating or promoting hair regrowth, in particular in the case of alopecia, or for reinforcing brittle hair, and/or for promoting growth of the nail and/or reinforcing the strength thereof. According to the invention, the cosmetic agent, or the active agent, is more particularly delivered topically in the form of a cosmetic composition containing it as one of its active agents, notably in solution or in dispersion in at least one cosmetically acceptable carrier suitable for application of said composition to the skin of the body or of the face.

Thus, the cosmetic composition comprises an effective amount of at least one cosmetic agent as defined above comprising an extract of the plant *Limnophila*, for obtaining the abovementioned desired cosmetic effect.

Another aspect of the invention is a cosmetic care method for preventing or delaying the appearance of the signs of skin ageing or reducing the effects thereof, said method being characterized in that it comprises the delivery, to at least one area concerned of the skin of the body or of the face, of an effective amount of at least one cosmetically acceptable agent comprising at least one extract of the plant of the *Limnophila* genus, as defined above or as resulting from the examples.

According to a first embodiment of the invention, said cosmetic care method comprises the application, to at least one part of the skin of the face or of the body displaying or liable to display signs of skin ageing, of a cosmetic composition, for example a cream or a serum, comprising, as one of its active agents, at least one extract of the plant *Limnophila*, for the purpose of obtaining an antiwrinkle effect, in particular through a phenomenon of cellular re-densifying of the epidermis, and in the hollow of the wrinkles, and through the acceleration or the maintenance of the renewal thereof. It is known that the phenomenon of cellular re-densifying of the epidermis becomes finer with age, while the cell renewal of the epidermis decreases with age.

According to another embodiment of the invention, said cosmetic care method comprises the application of a composition comprising, as one of its active agents, at least one extract of the plant *Limnophila* to areas of the skin exposed to sunlight, in order to reinforce the resistance of the keratinocytes of the basal layer of the epidermis to apoptosis in such a way as to reduce the cell loss which results therefrom at the basal layer and to thus limit photoageing. It is known that apoptosis is induced by the UVB rays of solar radiation.

Yet another aspect of the invention relates to a cosmetic care method for care of, or for reconstructing, the epidermis or the stratum corneum thereof notably which is damaged, in particular by ultraviolet radiation, said method being characterized in that it comprises the delivery, to at least one part of the skin of the face or of the body, of an effective amount of a cosmetically acceptable agent comprising at least one extract of the abovementioned plant belonging to the *Limnophila* genus, in particular an extract of the plant species *Limnophila conferta*.

Another aspect of the invention relates to a cosmetic care method aimed at restoring the functioning of the hair cycle, for preventing or slowing down hair loss, for promoting or accelerating hair regrowth, in particular in the case of alopecia, or for reinforcing brittle hair, the growth of the hair shaft resulting from the multiplication of the keratinocytes of the hair bulb, characterized in that it comprises the delivery, to at least one part of the scalp, of an effective amount of a cosmetically acceptable agent comprising an extract of the abovementioned plant belonging to the *Limnophila* genus, in particular an extract of the plant species *Limnophila conferta*.

Yet another aspect of the invention relates to a cosmetic care method for promoting growth of the nail and/or reinforcing the strength thereof, characterized in that it comprises the delivery, to the nail or at least a part of the surrounding area, of an effective amount of at least one cosmetically acceptable agent comprising at least one extract of the plant of the *Limnophila* genus, in particular a plant of the species *Limnophila conferta*.

The tests carried out by the inventors have shown that the properties of the extract of the invention can also be obtained or improved in cosmetic compositions in which the extract is combined with other active agents having cosmetic effects similar and/or complementary to the extract of the invention.

In particular, the *Limnophila* extract may be used with at least one other active agent which contributes to the maintenance and to the integrity of the structure of the skin.

According to a first embodiment, the composition comprising the extract according to the invention may also contain at least one other cosmetically acceptable agent, in particular which activates or stimulates the expression of survivin in the skin, said agent possibly being an isolated molecule or the product of an extraction method, and being advantageously chosen from forskolin or an extract containing it, such as an extract of *Coleus forskolii*, or else an extract of a plant of the *Lepechinia* genus, in particular of the plant species *Lepechinia caulescens*, or belonging to one of the plant species among *Nostoc commune, Scenedesmus dimorphus, Curcuma longa, Crocus sativus* and *Daniellia oliveri*.

The effectiveness of a cosmetic active agent according to the invention will be advantageously improved by molecules or extracts capable of stimulating the expression of the adhesion proteins, such as beta-1 integrins, of epidermal keratinocytes, and the adhesion itself of these cells (magnesium aspartate, manganese salts and derivatives, certain peptides recognized by the integrin, such as the arginine-glycine-aspartic acid sequence, certain growth factors such as KGF).

The activating effectiveness of a cosmetic active agent according to the invention may also be advantageously improved by means of molecules or extracts capable of inhibiting phosphodiesterases which degrade cAMP, such as methylxanthines, and in particular caffeine, and which result in an increase in the intracellular cyclic AMP level.

The compositions comprising a cosmetic agent as described above may also comprise one or more other active agents that may be chosen from substances having a skin-lightening activity; substances having a slimming activity; substances having a hydrating activity; substances having a calming, soothing or relaxing activity; substances having an activity that stimulates the microcirculation of the skin so as to improve the radiance of the complexion, in particular of the face; substances having a sebum-regulating activity for the care of greasy skin; substances for cleansing or purifying the skin; substances having a free-radical-scavenging activity; substances for reducing or delaying the effects of skin ageing, in particular the formation of wrinkles, through an activity aimed at promoting maintenance of the skin structure and/or at limiting degradation of the extracellular matrix of the superficial layers of the dermis and of the epidermis and/or at obtaining a skin-protecting, correcting or restructuring effect; substances having an anti-inflammatory activity.

In addition to the extract of the invention, said cosmetic composition comprises at least one cosmetically acceptable excipient which may be chosen from pigments, dyes, polymers, surfactants, rheology agents, fragrances, electrolytes, pH modifiers, antioxidants and preservatives, and mixtures thereof.

The cosmetic composition according to the invention may, for example, be a serum, a lotion, an emulsion, for example a cream, or else a hydrogel, preferably a mask, or may be in the form of a stick, or else of a patch, or else of a hygiene product for the scalp, such as a shampoo or a conditioner, or else a make-up product, in particular a composition intended to be applied to the nails, for example a nail varnish.

The process conditions for obtaining the *Limnophila* plant extract, in particular an extract of the species *Limnophila conferta*, may be the same as those described above or in Example 1 or 2.

According to one particular embodiment, the invention concerns a cosmetic composition containing at least one extract according to the invention as defined above, alone or in combination with other extracts, in solution or in dispersion in a cosmetically acceptable carrier compatible with topical application to the skin or the nails.

According to any one of the subjects of the invention, the agent according to the invention may be delivered topically in the form of a cosmetic composition comprising said agent as one of its active agents, said composition also comprising at least one cosmetically acceptable excipient, by application of this composition to the part of the body concerned.

Finally, another subject of the invention relates to a method for the in vitro culture of stem cells and/or of cells with a high clonogenic potential for the purposes of fundamental studies or of the production of cultured epidermis, such as reconstructed epidermis, for therapeutic purposes, for example, as in the case of a graft, following burns or ulcerative wounds which heal poorly, characterized in that it comprises the addition, to the culture medium, of an active agent comprising at least one extract of the plant of the *Limnophila* genus, in particular a plant of the species *Limnophila conferta*, in an effective amount for maintaining said stem cells, and/or said cells with a high clonogenic potential, in culture or for the production of epidermis.

According to one variant, the concentration of active agent (s) or of extract is between 0.001% and 5% by weight of the culture medium.

In addition, for any aspect of the invention, the term "effective amount" is intended to mean an amount which is at least equal to the amount necessary:

a) for preventing or delaying the appearance of the signs of skin ageing or slowing down the effects thereof;

b) for reconstructing the epidermis or the stratum corneum thereof, when it is damaged, in particular by ultraviolet radiation, and/or c) for restoring the functioning of the hair cycle, in order to prevent or slow down hair loss, to accelerate or promote hair regrowth, in particular in the case of alopecia, or to reinforce brittle hair, and/or d) for promoting growth of the nail and/or reinforcing the strength thereof, e) for maintaining stem cells, and/or cells with a high clonogenic potential, in culture in order to make it possible to conserve these cultures for a period of time sufficient to carry out the culturing under good conditions, and also to carry out the production of epidermis, when necessary.

In practice, this effective amount can be readily determined by those skilled in the art. In general, the effective concentration of agent comprising the extract according to the invention, or of extract, will be between 0.001% and 5% by weight, in particular between 0.01 and 3% by weight, of the composition or of the culture medium.

As regards the extract, for any aspect, the concentration will be expressed in weight of dry extract relative to the weight of the composition.

As demonstrated by specific tests which have been carried out and reported in Examples 1 and 2, the cosmetic agent according to the invention is effective in particular by stimulating, unexpectedly, the expression of survivin in the stem cells of the basal layer of the dermis or of the epidermis.

Other objectives, characteristics and advantages of the invention will emerge clearly from the explanatory description which follows and which is given in reference to several exemplary embodiments of the invention, given simply by way of illustration and which could not in any way limit the scope of the invention. In the examples, the temperature is in degrees Celsius, the pressure is atmospheric pressure, and the amounts or the percentages are given by weight, unless otherwise indicated.

EXAMPLES

Materials and Methods

1. Activity of an Extract of *Limnophila conferta* on the Expression of the Wild-Type (WT) Survivin Gene (Example 2)

The objective of these tests is to study the modulation of the expression of the wild-type (WT) survivin gene in normal human keratinocytes (NHKs) treated with an extract of *Limnophila conferta*. The WT survivin gene is one of the 5 known isoforms of the survivin gene.

The keratinocytes used are obtained from the skin of a 31-year-old Caucasian woman.

1.1 Cell Treatment

The NHKs are seeded into a Petri dish 100 mm in diameter, in a proportion of 1 500 000 cells per dish, in medium 1.48 hours after seeding, the cells are treated with an extract of *Limnophila conferta* (12.5 µg/ml) diluted in DMSO. The cells are recovered after 8 hours of treatment, so as to extract the total RNA therefrom.

1.2 Obtaining the Total RNA Using the EZ1 Extractor (Qiagen)

The cell culture medium is removed, and 500 µl of Qiazol (supplied in the kit) are added. The cell lysate is recovered in a 1.5 ml tube. The total RNA is extracted according to the supplier's protocol.

The total RNA solutions obtained are assayed, and the quality thereof is verified, using a 12-well microplate (RNA 6000 NanoChips) and a reagent kit (RNA 6000 Nano Reagents & Supplies).

The total RNA is brought into contact with an enzyme, DNAse, in order to eliminate the genomic DNA possibly present in the extraction.

0.5 µg of total RNA is brought into contact with 1 µl of 10× buffer and 1 µl of DNAse RQ1 (1 U/µl) and 7 µl of sterile water (reaction in 10 µl final volume) for 30 minutes at 37° C. The reaction is stopped by adding a stop solution for 10 minutes at 65° C., for inactivating the DNAse.

1.3 Reverse Transcription

1.3.1 RT-PCR Reagents

|  | Supplier |
|---|---|
| EZ1 RNA Tissue Mini Kit | Qiagen |
| RQ1 Rnase Free Dnase | Promega |
| Pd(N)$_6$ | Amersham Pharmacia |
| dNTP | Amersham Pharmacia |
| RNAse inhibitor | Promega |
| SuperScript II | Invitrogen |
| Kit Hyprobe | Roche Diagnostics |
| Primers | Eurogentec |
| Beta-2-m kit | Roche Diagnostics |
| Brilliant SybrGreen kit | Stratagene |

1.3.2 Protocol

The reaction begins by adding 0.5 µl of 20 mM dNTP and 1 µl of pd(N)$_6$ to 0.1 µg of DNAse-treated RNA (2.2 µl), the volume being completed with 8.3 µl of water. This is followed by a 5 minute incubation at 65° C., during which the secondary RNA structures are eliminated. The mixture is then again placed in ice, and 7 µl of reaction mixture containing the following are added:

5× buffer, which should be 1× final, i.e. 4 µl
100 mM DTT, 10 mM final, i.e. 2 µl
RNAsin, i.e. 1 µl.

The pd(N)$_6$, which are random hexanucleotides, bind specifically to all the RNAs during a hybridization step of 10 minutes at 25° C. After the addition of 1 µl of reverse transcriptase, the samples are incubated for 1 hour at 42° C., enabling the enzyme to synthesize the cDNA strands. This step is followed by denaturation for 15 minutes at 70° C., which is necessary for separation of the RNA-cDNA double strands.

1.4 Real-Time Quantitative PCR

The effect of the extract of *Limnophila conferta* is evaluated by real-time quantitative PCR with the Mx3000P system from Stratagene using the Brillant SybrGreen kit.

The composition of the reaction mixture is the following:

| Components | Volume (µl) | Final concentration |
|---|---|---|
| 10X core PCR buffer | 2.5 | 1X |
| 50 mM MgCl$_2$ | 2 | 4 mM |
| 20 mM dNTP | 1 | 0.8 mM |
| Sense primer (1/100th) | 2.5 | 500 nM |
| Antisense primer (1/100th) | 2.5 | 500 nM |
| 50% glycerol | 4 | 8% |
| DMSO | 0.75 | 3% |
| Taq DNA polymerase (5 U/µl) | 0.25 | 2.5 U |
| SYBR Green I' (1/3000th) | 1.25 | 0.167X |
| H$_2$O | 6.25 | qs 23 µL |

The major difference between conventional PCR and real-time quantitative PCR is linked to the incorporation of the SYBR Green during the elongation step. The fluorescence emitted by this compound when it is incorporated into the double-stranded DNA is proportional to the amount of product amplified and measured at the end of each cycle.

For each sample, the number of cycles for which the signal appears is determined by the software and, by virtue of a calibration line, the concentration in terms of number of copies of transcript is calculated.

For one test, the levels of expression of the WT survivin transcripts obtained are standardized relative to the value obtained for the beta-2-m housekeeping gene. This gene, the expression of which is constitutive and does not vary, makes it possible to do away with any variation in amounts between tests and in particular due to different RT efficiencies. The beta-2-m PCR is carried out using the LightCycler-h-β2m Housekeeping Gene Set kit.

2. Study of the Activity of an Extract of *Limnophila conferta* on the Expression of the Survivin Protein (Example 3)

The objective of the present study is to look at the modulation of the expression of the survivin protein in normal human keratinocytes (NHKs) by an extract of *Limnophila conferta*.

2.1 Cell Culture

The NHKs are cultured in 75 cm$^2$ flasks, in an incubator at 37° C. under a humid atmosphere containing 5% CO$_2$, in serum-free keratinocyte medium supplemented with EGF (Epidermal Growth Factor) and with BPE (Bovine Pituitary Extract) (KSFMc) (Gibco ref: 17005-034+37000-015). The cells are seeded (day D0) into 48-well microplates in a proportion of 50 000 cells in 500 µl of medium per well.

After incubating for 24 hours (day D1), the cells have become adherent and the treatment step is then carried out. The seeding medium is removed and the treatment medium, each containing the extract of *Limnophila conferta* in solution in a solvent (for example, DMSO) at the various concentrations, is then added to each culture well. A control is also prepared using this same solvent and in the same proportions.

A peak of survivin expression by the cells is observed after treatment for 16 hours. The wells are then rinsed with PBS. Half the wells of the microplate are used to lyse the keratinocytes and to assay the intracellular survivin. The other half of the wells of the microplate are used to assay the total proteins by the BCA method, which makes it possible to relate the amount of survivin assayed back to a unit amount of protein.

A phase of measuring the cytotoxicity of each plant extract tested is necessary beforehand, in order to be able to subsequently evaluate the effect of the extract at noncytotoxic doses.

To this end, the cytotoxic dose of the extract is determined by means of the XTT test (ref: Cell Proliferation Kit II, Roche Diagnostic). The tetrazolium salt (XTT reagent) is converted to formazan by the dehydrogenases located in the mitochondrial respiratory chain. Only the living cells, the respiratory chain of which is functional, are capable of producing formazan, an orange compound detected at 450 nm.

Each extract tested is diluted in order to prepare a doubling dilution range on a microplate, the concentration of extract of the test samples ranging from 50 mg/ml to 0.195 mg/ml. Each pre-prepared dilution is finally diluted to 1/1000th in the KSFM-C medium and is then brought into contact with the keratinocytes for 48 h, at which point the cytotoxicity test will be carried out.

2.2 Assaying the Survivin Protein

The activity of plant extracts of plants of the plant species *Limnophila conferta* with respect to survivin expression is evaluated. The survivin is assayed by means of an ELISA enzymatic immunoassay (ref: Duoset Survivin ELISA from R&D Systems) on cultures of normal human keratinocytes.

The total proteins are assayed by means of a BCA colorimetric test (reference: BC Assay Kit, Uptima Interchim), by measuring absorbance at 570 nm.

For the ELISA assay of survivin after treatment for 16 h, the wells are rinsed with PBS and then 100 µl/well of lysis buffer are added, followed by incubation for 10 minutes with gentle agitation. This buffer contains antiproteases, which prevent degradation of the proteins, including the survivin, during the cell lysis.

The ELISA microplate (reference Clear Microplate R&D systems DY992) is prepared. A standard range with human survivin is prepared from 0 to 2000 pg/ml under the same conditions as with the cell lysates. After the enzyme reaction has been blocked with sulphuric acid, the survivin is quantified by measuring the absorbance at 450 nm.

Example 1

Preparation of an Extract of Above-Ground Parts of *Limnophila conferta*

The plant material, available commercially from the supplier IDVP France, formed from above-ground parts comprising the stems and the leaves of *Limnophila conferta* in the dry state, is ground extemporaneously using a laboratory mill-mixer, to an average particle size of the order of 0.1 to 1 mm.

10 g of ground plant material are introduced into a 250 ml round-bottomed flask, into which 150 ml of an ethanol/water mixture (90/10 v/v) are added.

The round-bottomed flask surmounted by a bulb condenser is stirred magnetically in a thermostated bath, and then heated to the solvent reflux.

The reflux is maintained for 30 minutes with stirring.

Once the heating has stopped, the round-bottomed flask is allowed to cool to ambient temperature outside the bath.

The mixture is then vacuum-filtered through a Büchner funnel with a Whatman 70 µm GF/F filter and a tared flask; the filtrate 1 is thus obtained. The cake is washed on the Büchner funnel with 50 ml of extraction solvent; the filtrate 2 is obtained.

The two filtrates were combined and weighed.

The resulting filtrate is introduced into a pre-tared round-bottomed flask, and then concentrated to dryness on a rotary evaporator under vacuum in a water bath at a maximum temperature of 50° C.

The dry residue is quantified in order to obtain the extraction yield by mass, expressed as mass of dry extract obtained per 100 g of starting plant material in the dry ground state.

The extraction yield is 21%.

Example 2

Activity of an Extract of *Limnophila conferta* with Respect to the Expression of the Gene Encoding WT Survivin Normal human keratinocytes seeded, in duplicate, into 100 mm Petri dishes are treated, at sub-confluence for 8 hours, with the extract of *Limnophila conferta* prepared according to Example 1, diluted in DMSO to a concentration of 12.5 µg/ml. A control (without treatment) is also prepared. The amount of transcripts encoding the WT survivin gene measured for a sample is related back to the amount of transcripts encoding the invariant beta-2-m gene.

The results are indicated in Table I below:

TABLE I

| | Survivin Per $10^5$ copies beta-2-m | Mean | Confidence interval |
|---|---|---|---|
| Control (non-treated) | 441688 618640 507534 691577 | 564860 | 109430 |
| Limnophila | 942611 813240 672602 739916 | 792092 | 113305 |

Conclusion: the treatment with 12.5 µg/ml of *Limnophila* extract after 8 hours increases the amount of WT survivin gene transcripts by 40%. There is thus a statistically significant difference (p<0.05) compared with control (non-treated cells), which demonstrates that the extract of *Limnophila conferta* has a modulatory action on the expression of the WT survivin gene.

Example 3

Activity of an Extract of *Limnophila conferta* with Respect to the Expression of the Survivin Protein The dry extract prepared in Example 1 is diluted to the concentration of 12.5 mg/ml or to the concentration of 25 mg/ml in DMSO.

During the treatment on cells, the extract is added to the culture medium in order to obtain a final concentration at 0.1% v/v, i.e. 12.5 µg/ml for the first solution and 25 µg/ml for the second solution. A control is also prepared using this same solvent, with the final concentration of 0.1% v/v.

Table II below indicates the activity of the extract of Example 1 with respect to survivin, relative to the basal level of expression, represented by the solvent control, which constitutes 100%.

The result obtained is indicated in Table II below:

TABLE II

| Plant | Dose (μg/ml) | Survivin (pg/mg proteins) | % activation |
|---|---|---|---|
| Control | — | 600 | 100 |
| *Limnophila conferta* | 12.5 | 776 | 129.3 |
| *Limnophila conferta* | 25 | 889 | 148.1 |

Conclusion: the extract of *Limnophila conferta* significantly increases the expression of survivin by the keratinocytes, relative to the basal level of expression of the protein (controls).

Conclusion of Examples 2 and 3

The extract of *Limnophila conferta* stimulates the expression of the WT survivin transcripts, and also the expression of the survivin protein itself. The extract tested therefore acts positively both at the transcriptional level (RNA) and at the translational level (protein).

Example 4

Cosmetic Composition Comprising an Extract of the Above-Ground Parts of *Limnophila conferta*

The dry extract obtained in Example 1 is solubilized at 1% by mass in an ethanol/water mixture.

A solution at 1% by mass of dry extract is obtained, and is used in the cosmetic composition below:

| | |
|---|---|
| Plant extract of *Limnophila conferta* | 0.1% |
| Surfactant (Arlacel ® 165 VP) | 5% |
| 95% cetyl alcohol | 1% |
| Stearyl alcohol | 1% |
| Beeswax | 1.5% |
| Oil (Perleam ®) | 8.5% |
| Tri caprate/caprylate glycerides | 3% |
| Silicone oil (dimethicone 100 CS) | 1% |
| Polymer (Keltrol ®) | 0.35% |
| Sodium hydroxide | 0.04% |
| Tetrasodium EDTA powder | 0.1% |
| Preservatives | 0.5% |
| Water | qs 100 |

The cosmetic composition is prepared in the usual manner, well known to those skilled in the art, by mixing the various components in one or more steps.

This composition can be applied to the areas of the skin daily for several weeks in order to obtain the abovementioned cosmetic effects.

Example 5

Antiwrinkle Tonic Lotion Comprising an Extract of *Limnophila conferta*

The dry extract obtained in Example 1 is solubilized at 1% by mass in an ethanol/water mixture.

A solution at 1% by mass of dry extract is obtained, and is used in the cosmetic composition below:

| | |
|---|---|
| Plant extract of *Limnophila conferta* | 2% |
| Butylene glycol | 3% |
| EDTA | 0.1% |
| Solubilizing agent | 1% |
| Fragrance concentrate | 0.3% |
| Ethanol | 5% |
| UV screen (benzophenone-4) | 0.13% |
| Water | qs 100 |

The cosmetic composition is prepared in the usual manner, well known to those skilled in the art, by mixing the various components in one or more steps.

This composition can be applied daily to the areas of the skin comprising wrinkles, for several weeks, in order to obtain an effect of reduction or of complete disappearance of said wrinkles.

Example 6

Antiwrinkle Day Cream in the Form of an Emulsion Comprising an Extract of *Limnophila conferta*

The dry extract obtained in Example 1 is solubilized at 1% by mass in an ethanol/water mixture.

A solution at 1% by mass of dry extract is obtained, and is used in the cosmetic composition below:

| | |
|---|---|
| Plant extract of *Limnophila conferta* | 2% |
| Steareth-21 (Brij 721) | 2.5% |
| Glyceryl stearate (Tegrin) | 1.1% |
| Stearyl alcohol | 5% |
| Glycerol tri caprate/caprylate | 12.5% |
| Butylene glycol | 3% |
| Glycerol | 2% |
| Preservative | 0.5% |
| Fragrance concentrate | 0.5% |
| UV screen (octyl methoxycinnamate) | 7.5% |
| Water | qs 100 |

The cosmetic composition is prepared in the usual manner, well known to those skilled in the art, by mixing the various components in one or more steps.

This composition can be applied daily to the areas of the skin comprising wrinkles, for several weeks, in order to obtain an effect of reduction or of complete disappearance of said wrinkles.

What is claimed:

1. A cosmetic composition comprising a polar solvent plant extract of *Limnophilia conferta* wherein the cosmetic composition is in the form of a serum, a lotion, an emulsion, a cream, a hydrogel, a mask, a stick, a patch, a hygiene product for the scalp, a make-up product, or a nail varnish.

2. The composition according to claim 1, wherein said extract is an extract of the whole plant.

3. The composition according to claim 1, wherein said extract is an extract of a part of the plant, the part selected from the root, the rhizome, the stem, the leaves, the flowers, the seeds or the floral buds, and a mixture thereof.

4. The composition according to claim 1, wherein said extract is obtained from the leaves.

5. The composition according to claim 1, wherein said polar solvent extract is obtained by extracting the plant with a polar solvent or a mixture of polar solvents.

6. The composition according to claim 5, wherein the polar solvent or the mixture of polar solvents used for the extraction is water, a $C_1$-$C_4$ alcohol, a glycol, or a mixture thereof.

7. The composition of claim 6, wherein said $C_1$-$C_4$ alcohol is ethanol or butanol and said glycol is glycerol, butylene glycol and propylene glycol, or a mixture thereof.

8. The composition according to claim 6, wherein said solvent mixture is a mixture of at least one alcohol and of water, comprising at least 10% v/v of the alcohol, the remainder being made up of water.

9. The composition according to claim 8, wherein the solvent mixture is a mixture of water and of ethanol in a 50/50 v/v ratio.

10. The composition according to claim 6, wherein said solvent mixture is a mixture of at least one glycol and of water, comprising at least 10% v/v of the glycol, the remainder being made up of water.

11. The composition according to claim 10, wherein the solvent mixture is a mixture of water and of butylene glycol in a 50/50 v/v ratio.

12. The composition according to claim 1, wherein said extract is in the form of a powder prepared by lyophilization or atomization of said extract.

13. The composition according to claim 1, wherein the extract of the plant is absorbed on to a support that is porous or nonporous nylon powders, micas, or any lamellar mineral substance.

14. The composition of claim 1, wherein said composition is in solution or in dispersion in a cosmetically acceptable carrier compatible with topical application to the skin, scalp or nails.

15. The composition according to claim 1, further comprising at least one other active agent which contributes to the maintenance and the integrity of the skin structure.

16. The composition according to claim 1, wherein the extract is present in said composition at a concentration of between 0.001% and 5% by dry weight of extract relative to the weight of the composition.

17. The composition according to claim 1, wherein the extract is present in said composition at the concentration of between 0.01 and 3% by dry weight of extract relative to the weight of the composition.

18. The composition of claim 1, wherein said cosmetic composition is a shampoo or a conditioner.

19. A method for reconstructing the epidermis or the stratum corneum for the purpose of accelerating or promoting healing, comprising:
topically delivering to at least one area of the skin of the body and/or of the face, an effective amount of in the composition according to claim 1.

20. A method for restoring the functioning of the hair cycle, for preventing or slowing down hair loss, for accelerating or promoting hair regrowth, or for reinforcing brittle hair, comprising:
delivering to at least one zone of a scalp, an effective amount of the composition according to claim 1.

21. A method for promoting growth of a nail, reinforcing the strength of a nail, or both, comprising:
delivering to a nail, or at least a part of the area surrounding area the nail, an effective amount of the composition according to claim 1.

* * * * *